United States Patent [19]

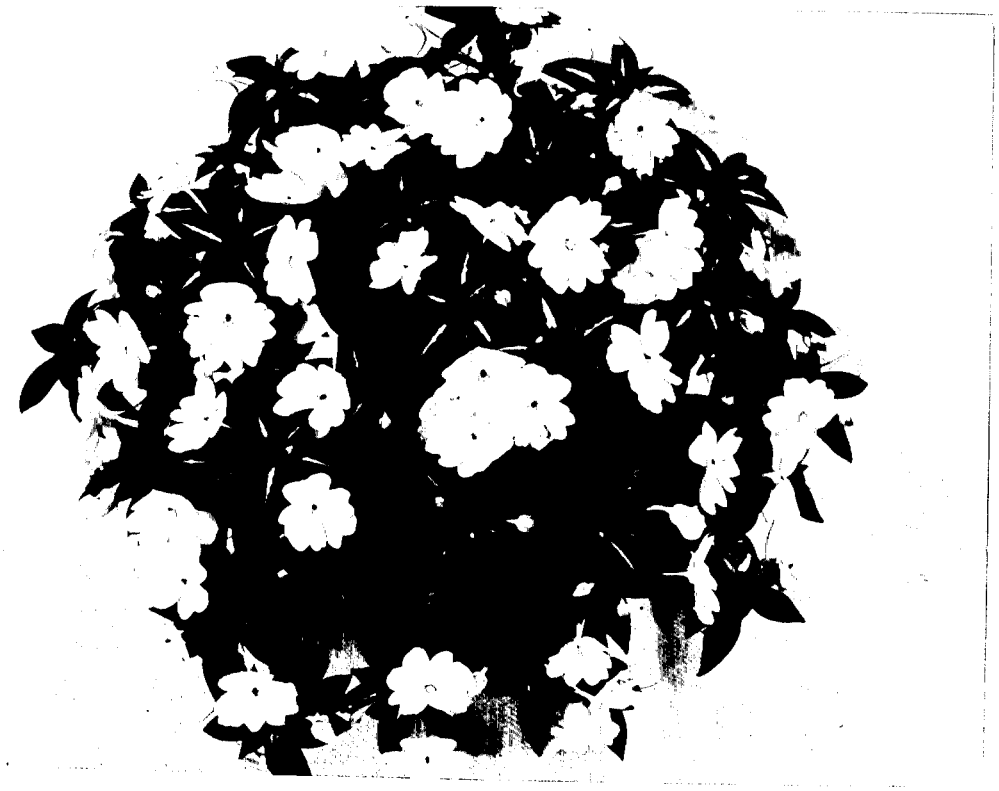

Mikkelsen

[11] Patent Number: Plant 5,775

[45] Date of Patent: Jul. 29, 1986

[54] IMPATIENS PLANT NAMED DAWN

[75] Inventor: James C. Mikkelsen, Ashtabula, Ohio

[73] Assignee: Mikkelsens, Inc., Ashtabula, Ohio

[21] Appl. No.: 663,037

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Dawn, having numerous salmon pink flowers, small leaf size, vigorous, self-branching mounded growth habit making it useful for pot, hanging basket and bedding plant use; and by its adaptability to various environments of use.

1 Drawing Figure

The present invention relates to a new and distinctive cultivar of New Guinea Impatiens plant, botanically known as Impatiens, and referred to by the cultivar name Dawn.

Dawn was developed by me in Ashtabula, Ohio, through controlled breeding by crossing Mikkelsen Seedling No. 82-581-1 (seed parent)×Mikkelsen Seedling No. 82-795-3 (pollen parent). Asexual reproduction by terminal or stem cuttings taken by me in Ashtabula, Ohio, has shown that the unique features of this new Impatiens are stabilized and are reproduced true to type in successive propagations.

The following characteristics distinguish the new impatiens from both its parent varieties and other cultivated impatiens of this type known and used in the floriculture industry:

1. Larger plant than Solared, Comet and Zenith. More compact than Corona, Twilight and Enterprise. Similar in size to Columbia, Quasar and Sunset. Solared, Corona and Columbia are disclosed in U.S. Plant Pat. Nos. 5,131, 5,184 and 5,126, respectively. Comet, Zenith, Twilight, Enterprise and Quasar are disclosed in pending applications, and Sunset is an unpatented cultivar.

2. Flower color is a salmon pink which is slightly lighter than Quasar and Sunfire but deeper than Columbia; flower color is deeper under winter conditions.

3. Flowers are numerous, being more abundant than in Columbia, but not as large. The flowers are similar in size to Meteor (unpatented) and Sunfire, but Dawn is much more floriferous. Flowers have excellent keeping qualities, and bloom from ground line to top of plant.

4. Cultivar is self-branching mound that makes it excellent for pot plants, hanging baskets or border plants.

5. Leaf color is similar to Solared and Columbia, but has the smallest leaf yet of any Mikkelsen cultivar introduced. There is basal variegation in the leaves, but not as heavy as in Solared or Quasar.

6. Plant and flowers have good low temperature tolerance as demonstrated by withstanding two nights of 2.2° C. after being planted outside in early May.

7. It is one of the first cultivars to flower, with only Quasar and Solared flowering earlier and with as many flowers.

8. Cultivar would make an excellent pot plant variety due to its mounded self-branching growth habit.

9. Excellent cultivar for further hybridization for pot plant and hanging basket plant use. Its small leaf size also would be useful in hybridizing for dense plant types.

The accompanying colored photograph taken in September 1984 illustrates the overall appearance in perspective view of Dawn, and showing the colors as true as it is reasonably possible to obtain in a colored reproduction of this type.

The following is a detailed description of my new Impatiens cultivar based on plants produced under commercial practices in Ashtabula, Ohio. The illustrated specimen was planted outside in full sun the first week of May from a 4" pot. It was dug the last week of August and moved into the greenhouse for three weeks before the photograph was taken. At that time, the plant was 30 cm tall and 50 cm in diameter. Color references are made to The Royal Horticultural Society Colour Chart except where general terms of ordinary dictionary significance are used.

Parentage: Mikkelsen Seedling No. 82-581-1×Mikkelsen Seedling No. 82-795-3.

Propagation:

(A) *Type cutting.*—Stem 15 mm long will develop 4 to 5 cm long in 18 to 21 days.

(B) *Time to root.*—8 to 10 days at 23° C. summer, 10 to 12 days at 20° C. winter.

(C) *Rooting habit.*—Large mass of fiberous roots from the stem.

Plant description:

(A) *Form.*—Symmetrical, mounded, compact flowering herb, with pale red stems.

(B) *Habit of growth.*—Vigorous, self-branching, compact, mounded, with continuous flowering.

(C) *Foliage description.*—Small, broad yellow-green leaves with some basal variegation. (1) Size: 4 to 5 cm long×2.25 to 2.5 cm wide. (2) Shape: Lanceolate to ovate with acuminate apex, acute base. (3) Texture: Rugose upper side, glabrous under side. (4) Margin: Finely serrated, finely ciliated. (5) Color: Young foliage, top side 146A, under side 147C. Mature foliage, top side 147A, under side 147B–148B. (6) Venation: Pinnate with green veins on mature leaves.

Flowering description:

(A) *Flowering habits.*—Flowers continuously from leaf whorl in progressive and orderly manner, taking 5 to 7 days from bud showing color to bloom; flowers last 2 to 3 weeks.

(B) *Natural flowering season.*—Indeterminant and continuous; quantity of flowers increases with increasing levels of light intensity and duration.

(C) *Flower buds.*—Ellipsoidal, flowers perfect, salmon pink spur 3.0 to 3.25 cm long on mature bud with throat behind ovary and originating from the major sepal.

(D) *Flowers borne.*—On individual short pedicels from whorl of five leaves, flowering progressively around the whorl as leaves and buds develop, and remaining just above the leaf canopy.

(E) *Quantity of flowers.*—Very floriferous; flowering is continuous so that tight buds to mature blooms are visible at the same time in large numbers.

(F) *Petals.*—(1) Shape: Heart shaped, top dominant, four overlapping, and symmeterical. (2) Color: Top side in summer when opening, 48C, fading to 52D to 49A; under side, 49A. (3) Number of petals: Five (5) in number. (4) Size of flowers: 5.0 cm to 6.0 cm in diameter.

(G) *Reproductive organs.*—(1) Stamens: Five (5) in number. (a) Anther shape: Hooded, color 48B. (b) Pollen color: Cream. (2) Pistels (a) Stigma shape: Five, segmented column-shaped, white in color. (b) Style color: Clear. (c) Ovaries: Five (5) in number, celled, size 5.5 mm until fertilized, green in color.

Disease resistance: No significant disease or insect problems have been seen to date.

I claim:

1. A new and distinct cultivar of New Guinea Impatiens plant named Dawn, as described and illustrated, and particularly characterized by its numerous salmon pink flowers, small leaf size, vigorous, self-branching mounded growth habit making it useful for pot, hanging basket, and bedding plant use; and by its adaptability to various environments of use.

* * * * *